United States Patent [19]

Bertola et al.

[11] Patent Number: 5,190,867
[45] Date of Patent: Mar. 2, 1993

[54] PROCESS FOR THE PREPARATION OF R-2,2-R$_1$,R$_2$-1,3-DIOXOLANE-4-METHANOL

[75] Inventors: Mauro A. Bertola; Arthur F. Marx, both of Delft; Hein S. Koger, Spaarndam; Volkert P. Claassen, Amsterdam, all of Netherlands; Gareth T. Phillips, Sittingbourne, United Kingdom

[73] Assignee: Shell International Petroleum Company, Ltd., London, England

[21] Appl. No.: 822,653

[22] Filed: Jan. 21, 1992

Related U.S. Application Data

[63] Continuation of Ser. No. 47,908, May 7, 1987, abandoned.

[30] Foreign Application Priority Data

May 8, 1986 [GB] United Kingdom ............... 8611238

[51] Int. Cl.$^5$ ..................... C12P 17/04; C12P 41/00
[52] U.S. Cl. .................................. 435/126; 435/280
[58] Field of Search ...................... 435/280, 123, 126

[56] References Cited

U.S. PATENT DOCUMENTS 4,772,749 9/1988 Karrenbauer et al. ............ 562/580
4,812,406 3/1989 Takahashi et al. ................. 435/280

Primary Examiner—Richard A. Schwartz
Assistant Examiner—Mary E. Mosher
Attorney, Agent, or Firm—Bierman and Muserlian

[57] ABSTRACT

Process for the preparation of R-2,2-R$_1$,R$_2$-1,3-dioxolane-4-methanol wherein R$_1$ and R$_2$ are H or alkyl groups or wherein R$_1$ and R$_2$ together with the carbon atom to which they are attached form a carbocyclic ring by subjecting a mixture of R- and S-2,2-R$_1$,R$_2$-1,3-dioxolane-4-methanol to the action of a micro-organism or substances derived therefrom having the ability for stereoselective consumption of S-2,2-R$_1$,R$_2$-1,3-dioxolane-4-methanol preferably until at least 80 wt % and more preferably all the S-2,2-R$_1$,R$_2$-1,3-dioxolane-4-methanol is consumed. Various micro-organisms of the genus Rhodococcus, Nocardia and Corynebacterium are disclosed as suitable for the purpose. The R-isomer is a valuable intermediate for stereospecific synthesis of various biologically active compounds including S-metoprolol.

29 Claims, No Drawings

PROCESS FOR THE PREPARATION OF R-2,2-$R_1$,$R_2$-1,3-DIOXOLANE-4-METHANOL

This is a continuation of Ser. No. 07/047,908, filed May 7, 1987, now abandoned.

The present invention relates to a process for the preparation of 2,2-$R_1$,$R_2$-1,3-dioxolane-4-methanol consisting predominantly of or substantially completely of R-isomer.

R-2,2-dimethyl-1,3-dioxolane-4-methanol is an important starting material for the preparation of agricultural and pharmaceutical products, see for example J. Jurczak et al., Tetrahedron vol. 42, no. 2, pp. 447–488 (1986).

In recent years, R-2,2-dimethyl-1,3-dioxolane-4-methanol has become of interest as an important starting compound for the preparation of many biologically active products and especially for the preparation of chiral drugs. The preparation of biologically active products in optically pure form using chiral starting materials is very advantageous, enabling precise planning and efficient realization of synthetic pathways. R-2,2-dimethyl-1,3-dioxolane-4-methanol is an important example of $C_3$-synthon and is used as starting compound for the preparation of many other $C_3$-synthons which are widely applied in organic synthesis as a chiral building block. For example, R-2,2-dimethyl-1,3-dioxolane-4-methanol can be used in the synthesis of other chiral synthons, monosaccharides, their derivatives and other polyhydroxylsystems, and biologically active products of more complex structure. Examples of the syntheses of more complex structures are the preparation of β-blockers or optically pure β-lactam systems.

Therefore there is still a great need for a process, usuable on an industrial scale giving rise to economically attractive yields for the stereoselective preparation of the R-stereoisomer of 2,2-dimethyl-1,3-dioxolane-4-methanol. The present invention provides such a process. It has been found that the stereoselective preparation of the R-stereoisomer can be advantageously carried out using micro-organisms of substances derived therefrom. Moreover it has been found that the S-stereoisomer of 2,2-$R_1R_2$-dioxolane-2-methanol may be advantageously converted into R-2,2-$R_1R_2$-1,3-dioxolane-4-carboxylic acid using these micro-organisms or substances derived therefrom.

The present invention provides a process for the preparation of 2,2-$R_1$,$R_2$-1,3-dioxolane-4-methanol enriched in R-isomer wherein $R_1$ and $R_2$ are H or alkyl groups, optionally substituted or branched or wherein $R_1$ and $R_2$ together with the carbon atom to which they are attached form a carbocyclic ring, optionally substituted, which comprises subjecting a mixture of R- and S-2,2-$R_1$,$R_2$-1,3-dioxolane-4-methanol to the action of a micro-organism or substances derived therefrom having the ability for stereoselective consumption of S-2,2-$R_1$,$R_2$-1,3-dioxolane-4-methanol for a period of time such that S-2,2-$R_1$,$R_2$-1,3-dioxolane-4-methanol in the mixture is consumed to give a 2,2-$R_1$, $R_2$-1,3-dioxolane-4-methanol enriched in R-isomer. Suitably at least 80 wt %, preferably 90 wt % and more preferably substantially all of S-2,2-$R_1$,$R_2$-1,3-dioxolane-4-methanol is consumed, to give 2,2-$R_1$,$R_2$-1,3-dioxolane-4-methanol enriched in R-isomer or consisting of substantially pure R-isomer. The enriched 2,2-$R_1R_2$-1,3-dioxolane-4-methanol enriched in R-isomer is at least partly isolated and/or used as starting material for the preparation of other optically active compounds. Advantageously $R_1$ and $R_2$ are alkyl groups containing less than 6 carbon atoms or wherein the carbocyclic ring contains less than 8 carbon atoms. Preferably $R_1$ and $R_2$ are identical. In this way no extra asymmetry is brought in the compounds. More preferably $R_1$ and $R_2$ are an alkyl group containing 1–3 carbon atoms or together with the carbon atom to which they are attached form a carbocyclic ring containing 5 or 6 carbon atoms.

As hereinbefore described the mixture of R and S isomers of 2,2-$R_1$,$R_2$-1,3-dioxolane-4-methanol may be converted into 2,2-$R_1$,$R_2$-1,3-dioxolane-4-methanol enriched in R-isomer. In this way only part of the mixture can be used in further reactions, for example starting with a 50 wt % R- and 50 wt % S-mixture only half of the 2,2-$R_1$,$R_2$-1,3-dioxolane-4-methanol becomes avaiḷabe in a useful way. According to an embodiment of the invention, the S-2,2-$R_1R_2$-1,3-dioxolane-4-methanol is advantageously converted into R-2,2-$R_1$,$R_2$-1,3-dioxolane-4-carboxylic acid.

In this way not only the preparation of 2,2-$R_1$,$R_2$-1,3-dioxolane-4-methanol enriched in R-isomer is possible, but at the same time 2,2-$R_1$,$R_2$-1,3-dioxolane-4-carboxylic acid enriched in R-isomer may be obtained. In this way substantially all the R and S-2,2-$R_1$,$R_2$-1,3-dioxolane-4-methanol may be separated and may be used. The 2,2-$R_1$,$R_2$-1,3-dioxolane-4-carboxylic acid enriched in R-isomer may be used as starting compound for the preparation of many biologically active products or may be converted to the 2,2-$R_1$,$R_2$-1,3-dioxolane-4-methanol enriched in S-isomer, which is an important starting compound as well.

By the term "micro-organisms having the ability for stereoselective consumption" is meant, for example, bacteria, yeasts, fungi. Suitable bacteria are, for example, micro-organisms belonging to the genus Nocardia, to the genus Rhodococcus, to the genus Mycobacterium or to the genus Corynebacterium.

Also micro-organisms, which have obtained the ability for consumption of S-2,2-$R_1$,$R_2$-1,3-dioxolane-4-methanol through the introduction of novel genetic material are embodied by the term "micro-organism, having the ability for stereoselective consumption".

This can be accomplished by transferring the cloned gene encoding a polypeptide responsible for the stereoselective consumption, an enzyme, from any of the screened micro-organisms to another micro-organism, particularly to Escherichia coli. Other micro-organisms may be belonging to the genus Saccharomyces, Kluyveromyces, Bacillus, Nocardia, Rhodococcus, Escherichia and Corynebacterium. Cloned genes may be selected for their ability to encode an enzyme capable of consuming of S-2,2-$R_1$,$R_2$-1,3-dioxolane-4-methanol. preferably S-2,2-dimethyl-1,3-dioxolane-4-methanol, Alternatively they may be selected by cross-hybridization with an already selected gene encoding an enzyme for the stereoselective consumption.

The micro-organisms may advantageously be immobilized for example on a polymer gel. This can be done with living cells, killed cells and/or resting cells, but alternatively with suitable enzymes derived therefrom, which may be purified to a certain extent if a higher specific activity is needed.

Therefore by the term "micro-organisms or substances derived therefrom" is meant the micro-organisms, killed, alive or resting, extracts therefrom, optionally concentrated or purified. For example, enzymes optionally in combination with, for example, artificial or natural co-factors, may be used. No fermentatively active cells may be used for the consumptions of the S-2,2-$R_1$,$R_2$-1,3-dioxolane-4-methanol. It is found that enzymes derived from the cells or killed cells may consume the S-isomer under suitable conditions. The micro-organisms or substances derived therefrom may be used several times and are active for at least 2 weeks. Even without co-substrate (for example glucose) the micro-organisms may remain active. The enrichment in R-isomer of R-2,2-$R_1$,$R_2$-1,3-dioxolane-4-methanol may take place in suitable buffers (for example 3-(N-morpholino)propane sulfonic acid, tris(hydroxymethyl)aminomethane or potassium phosphate) as well as in physiological salts. After being stored the induced cells are found to be directly capable to transform the enrichment in R-isomer.

More particularly the micro-organism for the consumption of S-2,2-$R_1$,$R_2$-1,3-dioxolane-4-methanol include cultures of *Rhodococcus equi, Rhodococcus rhodochrous, Rhodococcus erythropolis, Corynebacterium equi, Corynebacterium alkanum* (a sample of this species is deposited with the ATCC under the accession number of 21194), *Corynebacterium hydrocarboclastus* (a sample of this species is deposited with the ATCC under the accession number of 15108), *Corynebacterium species* T 1300 (a sample of this species is deposited with the CBS under the accession number of 267.87), *Corynebacterium species* DS 5122 (a sample of this species is deposited with the CBS under the accession number of 265.87), *Nocardia erythropolis, Norcardia corallina* (a sample of this species is deposited with the ATCC under the accession number of 31338), *Nocardia canicruria* (a sample of this species is deposited with the ATCC under the accession number 31548), *Nocardia paraffinae* (sample of this species is deposited with the NCIB under the accession number of 11277), *Nocardia species* DS 5123 (a sample of this species is deposited with the CBS under the accession number of 266.87), *Nocardia aurantia* (a sample of this species is deposited with the NCIB under the accession number of 9557), *Nocardia calcarea* (a sample of this species is deposited with the NCIB under the accession number of 8863), *Nocardia cathaarde* T 985 (a sample of this species is deposited with the CBS under the accession number of 268.87), *Nocardia globerula* (a sample of this species is deposited with the NCIB under the accession number of 9159), *Nocardia ragosa* (a sample of this species is deposited with the NCIB under the accession number of 8926) and *Mycobacterium rhodochrous* (a sample of this species is deposited with the NCIB under the accession number of 11061).

Advantageously cultures of the *Rhodococcus equi* include cultures of species *Rhodoccus equi* (a sample of this species is deposited with the IFO under the accession number of 03730) and species *Rhodococcus equi* (a sample of this species is deposited with the NCIB under the accession number of 12035). Advantageously cultures of the *Rhodococcus rhodochrous* include cultures of species *Rhodococcus rhodochrous* (a sample of this species is deposited with the NCIB under the accession number of 9703) and species *Rhodococcus rhodochrous* (a sample of this species is deposited with the ATCC under the accession number of 21197). Advantageously cultures of the *Rhodococcus erythropolis* include cultures of species *Rhodococcus erythropolis* SCL 38-2 (a sample of this species is deposited with the CBS under the accession number of 179.86 on Apr. 18, 1986), species *Rhodococcus erythropolis* SCL 38-2R (a sample of this species is deposited with the CBS under the accession number of 180.86 on Apr. 18, 1986) and species *Rhodococcus erythropolis* SCL 38-2S (a sample of this species is deposited with the CBS under the accession number of 181.86 on Apr. 18, 1986. Advantageously cultures of the *Corynebacterium equi* include cultures of species *Corynebacterium equi* A 2362 (a sample of this species is deposited with the CBS under the accession number of 264.87) and species *Corynebacterium equi* A 2431 (a sample of this species is deposited with the CBS under the accession number of 263.87). Advantageously cultures of the *Nocardia erythropolis* include cultures of species *Nocardia erythropolis* T 487 (a sample of this species is deposited with the NCIB under the accession number of 9158), species *Nocardia erythropolis* (a sample of this species is deposited with the DSM under the accession number of 743) and species *Nocardia erythropolis* (a sample of this species is deposited with the ATCC under the accession number of 4277).

The R-2,2-$R_1$,$R_2$-1,3-dioxolane-4-methanol produced according to the present invention may be used as a starting material for the production of other optically active compounds. An important possibility is the production of chrial drugs.

It will be appreciated by everyone skilled in the art that any suitable process may be used to convert S and R-2,2-$R_1R_2$-1,3-dioxolane-4-methanol in the optically active compounds.

Examples which illustrate the use of S and R-2,2-dimethyl-1,3-dioxolane-4-methanol for the preparation of optically active compounds are known from, for example, J. Jurczak et al, Tetrahedron report number 195, Tetrahedron 42 (1986), p. 447–488 and the Technical Information Bulletin 225, September 1983 of Janssen Chimica (Belgium).

The optically active compounds may be used in pharmaceutical or agricultural products.

According to a preferred embodiment of the process of the present invention a micro-organism having the ability for stereoselective consumption of S-2,2-$R_1$,$R_2$-1,3-dioxolane-4-methanol has to be cultured for about 0.5 to 10 days, whereafter the cells of the micro-organisms are suspended in a liquid nutrient medium and the mixture of R- and S-2,2-$R_1$,$R_2$-1,3-dioxolane-4-methanol is subjected to the action of the cells.

After the abovementioned cultivation for about 0.5 to 10 days the cells may be isolated from the culturing medium before suspending the cells in the liquid nutrient medium.

To grow the micro-organism used for the selective consumption of S-2,2-$R_1$,$R_2$-1,3-dioxolane-4-methanol, ordinary culture mediums containing an assimilable carbon source (for example glucose, lactate, sucrose, etc.), an assimilable nitrogen source (for example ammonium sulphate, ammonium nitrate, ammonium chloride, etc.), with an agent for an organic nutrient source (for example yeast extract, malt extract, peptone, meat extract, etc.) and an inorganic nutrient source (for example phosphate, magnesium, potassium, zinc, iron and other metals in trace amounts) may be used.

A Jap medium optionally enriched with one or more ingredients may be used as a suitable culture medium. A Jap medium of the following composition may be used: soybean flour (30 g/l), sodium nitrate (7.5 g/l), ferrous sulphate.7$H_2O$ (0.28 g/l), sodium citrate (6 g/l) and fructose (12.5 g/l), the pH adjusted to 7.2. Before use the medium is conveniently sterilized for 20 minutes at 120° C.

Another preferred culture medium is a YPD-medium optionally enriched with one or more ingredients. A YPD medium consisting of 20 g/l bactopeptone, 10 g/l yeast extract and 20 g/l glucose may be used. Before use, the medium is conveniently sterilized for 30 minutes at 110° C.

Another preferred culture medium is a GYMB-medium optionally enriched with one or more ingredients. A GYMB-medium of the following composition may be used: glucose (10 g/l), peptone (5 g/l), yeast extract (3 g/l), malt extract (3 g/l), which is conveniently sterilized for 20 minutes at 120° C. before use.

Another preferred culture medium is a medium 3310 optionally enriched with one or more ingredients. A medium 3310 of the following composition may be used: $(NH_4)_2SO_4$ (10 g/l), NaCl (1 g/l), $MgSO_4.7H_2O$ (1 g/l), $K_2HPO_4$ (5 g/l), $MnSO_4.3H_2O$ (2.5 mg/l), $ZnSO_4.7H_2O$ (2.5 mg/l), $FeSO_4.7H_2O$ (2.5 mg/l), $CaCl_2$ (12.5 mg/l), $CuSO_4.5H_2O$ (0.75 mg/l), $CoCl_2.6H_2O$ (0.75 mg/l), $H_3BO_3$ (0.25 mg/l), $Na_2MoO_4.2H_2O$ (0.275 mg/l), KI (0.5 mg/l), Ca-pantothenate (0.8 mg/l), inositol (4 mg/l), nicotinic acid (0.8 mg/l), thiamin HCl (0.8 mg/l), pyridoxin.HCl (0.8 mg/l), p-aminobenzoic acid (0.4 mg/l), riboflavin (0.4 mg/l), folic acid (0.02 mg/l), biotin (4 μg/l). Before use the medium is conveniently sterilized for 20 minutes at 120° C. Thereafter glucose (for example 50 g/l) sterilized for 30 minutes at 110° C. is added.

Another preferred culture medium is a skimmed milk medium optionally enriched with one or more ingredients, for example, a skimmed milk medium containing: 10% skimmed milk from skimmed milkpowder, which is conveniently sterilized for 30 minutes at 110° C. before use.

Examples of enrichments to the skimmed milk medium include 0.5% lactate or PSIII salts or combinations thereof. PSIII salt medium of the following composition can be used: potassium dihydrogen phosphate (2.1 g/l), ammonium monohydrogen phosphate (1.0 g/l), ammonium sulphate (0.9 g/l), potassium chloride (0.2 g/l), sodium citrate (0.29 g/l), calcium sulphate.$2H_2O$ (0.005 g/l), magnesium sulphate.$7H_2O$ (0.2 g/l), ammonium ferrous sulphate.$6H_2O$ (2.5 mg/l), zinc sulphate.$7H_2O$ (0.5 mg/l), manganese chloride.$4H_2O$ (0.3 mg/l), copper sulphate.$5H_2O$ (0.15 mg/l), cobalt chloride.$6H_2O$ (0.15 mg/l), ortho-boric acid (0.05 mg/l), sodium molybdate.$2H_2O$ (0.055 mg/l) and potassium iodide (0.1 mg/l), the pH was adjusted at 6.8. Before use the PSIII salt medium is conveniently sterilized for 30 minutes at 120° C.

A temperature of 0° to 45° C. and a pH of 3.5 to 9 is preferably maintained during the growth of the micro-organism. Preferably the micro-organism is grown at a temperature of 20° to 37° C. and at a pH of 5 to 9. The aerobic conditions required during the growth of the micro-organsims can be provided by any of the well-established procedures, provided that the supply of oxygen is sufficient to meet the metabolic requirement of the micro-organisms. This is most conveniently achieved by supplying oxygen, suitably in the form of air and optionally at the same time shaking or stirring the reaction liquid. During the consumption of S-2,2-$R_1$, $R_2$-1,3-dioxolane-4-methanol by the micro-organism, the micro-organism might be in a growing stage using an abovementioned ordinary culture medium.

During the consumption of S-2,2-$R_1$,$R_2$-1,3-dioxolane-4-methanol by the micro-organism, an ordinary culture medium may be used containing an assimilable carbon source when required (for example glucose, lactate, sucrose, etc.), an assimilable nitrogen source when required (for example ammonium sulphate, ammonium nitrate, ammonium chloride, etc.), with an organic nutrient source when required (for example yeast extract, malt extract, peptone, meat extract, etc.) and in inorganic nutrient source when required (for example phosphate, magnesium, potassium, zinc, iron and other metals in trace amounts).

Advantageously, during the enrichment of R-isomer, a Jap medium, a YPD medium, a Medium 3310 or a skimmed milk medium (as described above) optionally enriched with one or more ingredients can be used. Preferably a GYMB medium (as described above) optionally enriched with one or more ingredients is used.

The micro-organism can be kept in the non-growing stage, for example, by exclusion of the assimilable carbon source or by exclusion of the nitrogen source. A temperature of 0° to 45° C. and a pH of 3.5 to 9 can be maintained during this stage.

Preferably the micro-organisms are kept at a temperature of 20° to 37° C. and a pH of 5 to 9. The aerobic conditions required during this stage can be provided according to any of the well-established procedures, provided that the supply of oxygen is sufficient to meet the metabolic requirement of the micro-organisms. This is most conveniently achieved by supplying oxygen, suitably in the form of air and optionally, at the same time, shaking or stirring the reaction liquid. The R- and any remaining S-2,2-$R_1$,$R_2$-1,3-dioxolane-4-methanol after transformation as mentioned above, can then be recovered and purified according to any of the procedures known per se for such products.

The micro-organisms can be kept on agar slants, frozen in 50% glycerol or lyophilised. If required, precultures of these micro-organisms can be made according to any of the well-established procedures, for example (Brain Heart infusion), the micro-organisms can be incubated in bouillon or in BHI for 24 hours at 30° C. in a rotary shaker. A bouillon medium of the following composition can be used: Lab Lemco L 29 (meat extract, Oxoid ®) (9 g/l), Bactopeptone (10 g/l) and sodium chloride (5 g/l), the pH adjusted to 7.6. Before use this medium is conveniently sterilized for 20 minutes at 120° C.

A BHI (brain-heart infusion) medium containing 0.037 g/l BHI (Oxoid ®), the pH adjusted to 7.0, can be used. Before use this medium is conveniently sterilized for 20 minutes at 120° C.

Preferably a micro-organism is used which uses during the consumption of S-2,2-$R_1$,$R_2$-1,3-dioxolane-4-methanol, the S-2,2-$R_1$,$R_2$-1,3-dioxolane-4-methanol.

The present invention will be further illustrated with reference to the following Examples.

EXAMPLE 1

*Rhodococcus equi* NCIB 12035 was grown for 48 hours at 30° C., in several 500 ml baffle flasks containing 100 ml of 10% skimmed milk medium. Thereafter 120 μl of RS-2,2-dimethyl-1,3-dioxolane-4-methanol was added to each flask and incubated further for 24, 48 and 96 hours. At each time indicated 3 flasks (300 ml culture) were extracted using a continuous extraction procedure. The extracts were purified on a silicagel column and the optical rotation was measured in a polarimeter in 1 or 10 cm pathlength cell (volume 0.5–5 ml) maintained at 22° C. and ethanol as solvent.

Rotations were recorded at 589 nm (Sodium D-line).

The enantiomeric distributions were measured with NMR using an Europium (HFC)$_3$ shift reagent.

The results are presented in Table 1 here below.

TABLE 1

| Incubation time (h) | Quantity 2,2-dimethyl-1,3-dioxolane-4-methanol (mg) | ($\alpha_D$) | Enantiomer distribution % R | % S |
|---|---|---|---|---|
| 24 | 95.5 | −5 | 75 | 25 |
| 48 | 61.1 | −9.7 | 100 | 0 |
| 96 | 54.0 | −10.1 | 100 | 0 |

EXAMPLE 2

A *Rhodococcus erythropolis* SCL38-2 (CBS 179.86) was grown as described in Example 1 and after the addition of 120 µl of RS-2,2-dimethyl-1,3-dioxolane-4-methanol further incubated for 12, 24 and 48 hours. Extraction, purification and measurements of the 2,2-dimethyl-1,3-dioxolane-4-methanol were made as described in Example 1.

The results are presented in Table 2 here below.

TABLE 2

| Incubation time (h) | Quantity 2,2-dimethyl-1,3-dioxolane-4-methanol (mg) | ($\alpha_D$) | Enantiomer distribution % R | % S |
|---|---|---|---|---|
| 12 | 93.6 | −8.8 | 93 | 7 |
| 24 | 77.8 | −10.4 | 100 | 0 |
| 48 | 69.1 | −9.8 | 100 | 0 |

EXAMPLE 3

*Rhodococcus erythropolis* SCL 38-2 (CBS 179.86) was first grown for 48 hours at 30° C. in several 100 ml baffle flasks containing 25 ml 10% skimmed mild medium after which RS-2,2-dimethyl-1,3-dioxolane-4-methanol was added to the cultures. To each series of the flasks was added a different starting concentration of RS-2,2-dimethyl-1,3-dioxolane-4-methanol 1.2, 2.4, 4.8 and 9.6 g/l respectively. At certain time-points samples of a flask of each series was taken, extracted and analyzed. It appeared that up to 4.8 g/l RS-2,2-dimethyl-1,3-dioxolane-4-methanol half of the added amount, is consumed within 48 hours. At 9.6 g/l it takes more than 96 hours before half of the RS-2,2-dimethyl-1,3-dioxolane-4-methanol is consumed. Since it was assumed that most of the 2,2-dimethyl-1,3-dioxolane-4-methanol consumed would have the S-configuration, a new experiment based on the experience obtained above was set up in order to prepare larger quantities of R-2,2-dimethyl-1,3-dioxolane-4-methanol.

A total of 5.76 g RS-2,2-dimethyl-1,3-dioxolane-4-methanol was divided over twelve 500 ml baffle flasks containing 100 ml 10% skimmed milk in which the *Rhodococcus erythropolis* SCL 38-2 had grown for 48 hours. The cultures were then further incubated at 30° C. for 96 hours. From the total volume of ca. 1.2 l the remaining 2,2-dimethyl-1,3-dioxolane-4-methanol was extracted and purified as described in Examples 1 and 2.

An amount of 1.5 g 2,2-dimethyl-1,3-dioxolane-4-methanol was isolated and NMR measurements showed it to be of the R-configuration, 100% enantiomeric pure.

EXAMPLE 4

In an experiment the *Rhodococcus erythropolis* SCL 38-2 (CBS 179.86) was grown at 30° C. for 48 hours in three 2 l baffle flasks containing 500 ml 10% skimmed milk. A total of 7.2 g RS-2,2-dimethyl-1,3-dioxolane-4-methanol was divided over the cultures and incubated further for 96 hours. Extraction and purification of the remaining 2,2-dimethyl-1,3-dioxolane-4-methanol was performed as described in Example 1, 2 and 3.

An amount of 1.4 g R-2,2-dimethyl-1,3-dioxolane-4-methanol was recovered, according to NMR measurements 100% enantiomer pure.

Example 5

The three variant forms of *Rhodococcus erythropolis* SCL 38-2, SCL 38-2S and SCL 38-2R, respectively, were each grown in twice 100 ml skimmed milk as described in Example 1 for 48 hours. The biomass dry weights were determined and found to be equal for all three forms. The cultures were divided in portions of 30 ml and put in 100 ml baffle flasks. In this way the cultures of each form were split in five different cultures of 30 ml. 60 µl of RS-2,2-dimethyl-1,3-dioxolane-4-methanol were added to these cultures and incubated further. At different time points, (see Table 3), one culture of each form was taken, extracted and the remaining 2,2-dimethyl-1,3-dioxolane-4-methanol was analysed. The enantiomeric distribution was determined by formation of diastereoisomers with N,O-bis-(trimethylsilyl)trifluoracetamide (BSTFA) which were separated on a chiral complexation column. No clear differences were found between the three forms.

TABLE 3

| assay time hour | SCL 38-2R | | | | SCL 38-2S | | | | SCL-38 | | | |
|---|---|---|---|---|---|---|---|---|---|---|---|---|
| | quantity left over g/l | | enantiomeric distribution | | quantity left over g/l | | enantiomeric distribution | | quantity left over g/l | | enantiomeric distribution | |
| | R | S | % R | % S | R | S | % R | % S | R | S | % R | % S |
| 0 | 0.55 | 0.55 | 50 | 50 | 0.57 | 0.54 | 50 | 50 | 0.55 | 0.55 | 50 | 50 |
| 3 | 0.57 | 0.57 | 50 | 50 | 0.55 | 0.55 | 50 | 50 | 0.54 | 0.53 | 50 | 50 |
| 6 | 0.57 | 0.49 | 54 | 46 | 0.57 | 0.52 | 53 | 47 | 0.56 | 0.47 | 55 | 45 |
| 8 | 0.57 | 0.38 | 60 | 40 | 0.57 | 0.39 | 59 | 41 | 0.57 | 0.35 | 62 | 38 |
| 24 | 0.46 | 0.00 | 100 | 0 | 0.49 | 0.00 | 100 | 0 | 0.45 | 0.00 | 100 | 0 |

EXAMPLE 6

This example describes the preparation of S-metoprolol, a beta-blocker from R-2,2-dimethyl-1,3-dioxolane-4-methanol. This example demonstrates the possibility of using R-2,2-dimethyl-1,3-dioxolane-4-methanol as a starting material for the synthesis of other optically active materials.

Preparation of
S-2,2-dimethyl-4-(methanesulphonyloxymethyl)-1,3-dioxolane from
R-2,2-dimethyl-1,3-dioxolane-4-methanol A mixture of 1.2 ml (15.5 mmole) of methanesulphonyl chloride and 4 ml of methylene chloride was added in 5 min. to a stirred and cooled mixture of 7 ml of methylene chloride, 2.6 ml (18.7 mmole) of triethylamine and 1.81 g (13.7 mmole) R-2,2-dimethyl-1,3-dioxolane-4-methanol (which was optically pure by NMR). This R-isomer was prepared by the procedure described in Examples 1-5.

Stirring was continued at 22° C. for 1½ hours and next more methanesulphonyl chloride (0.15 ml) and triethylamine (0.5 ml) were added. After standing in the refrigerator overnight the mixture was shaken with methylene chloride and 1N sodium bicarbonate solution. The organic layer was washed with 1N sodium bicarbonate solution, filtered and evaporated to give 2.78 g of S-2,2-dimethyl-4-(methanesulphonyloxymethyl)-1,3-dioxolane as brown oil, which was used as such.

Preparation of
S-2,2-dimethyl-4-[p-(2-methoxyethyl)-phenyloxymethyl]-1,3-dioxolane from
S-2,2-dimethyl-4-(methanesulphonyloxymethyl)-1,3-dioxolane p-(2-methoxyethyl)-phenol (2.2 g, 14.47 mmole) was added to a cooled (to keep the reaction mixture below 100° C.) and stirred mixture of 10 ml of dry N,N-dimethylformamide and 0.38 g (15.8 mmole) of sodium hydride.

Next 2.78 g of crude S-2,2-dimethyl-4-(methanesulphonyloxymethyl)-1,3-dioxolane were added and the mixture was stirred and heated in an oil bath of 100° C. for 1½ hours.

After cooling to 22° C. the mixture was poured into 1M sodium bicarbonate and extracted with ether. The ether extract was washed with 1N sodium hydroxide, 1M sodium bicarbonate, brine, dried with magnesium sulphate, filtered and evaporated to give 3.20 g of S-2,2-dimethyl-4-[p-(2-methoxyethyl)-phenyloxymethyl]-1,3-dioxolane as an oil, which was used as such.

Preparation of
S-3-[p-(2-methoxyethyl)-phenoxy]-1,2-propanediol from
S-2,2-dimethyl-4-[p-(2-methoxyethyl)-phenyloxymethyl]-1,3-dioxolane A mixture of 3.20 g of crude S-2,2-dimethyl-4-[p-(2-methoxyethyl)-phenyloxymethyl]-1,3-dioxolane, 15 ml of methanol, 10 ml of water and 0.5 ml of 36% hydrochloric acid was stirred at 22° C. for 1 hour. After the addition of another 0.5 ml of 36% hydrochloric acid stirring was continued for ½ hour and next 10 ml of 1M sodium carbonate were added and the mixture concentrated in vacuum.

The residue was extracted with ether and the extracted was washed with brine, filtered and evaporated to give 2.60 g of the crude title compound as an oil, which was used as such.

Preparation of
R-1-bromo-2-acetoxy-3-[p-(2-methoxyethyl)-phenyloxy]-propane from
S-3-[p-(methoxyethyl)-phenoxy]-1,2-propanediol A mixture of 2.6 g of crude S-3-[p-(methoxyethyl)-phenyloxy]-1,2-propanediol and 10 ml of 33% hydrobromic acid in acetic acid was stirred at 22° C. for 1¼ hours.

Next the mixture was poured into 100 ml of 1M sodium carbonate and extracted with diethyl ether. The extract was washed with 1M sodium carbonate, brine, dried with magnesium sulphate, filtered and evaporated to give 3.65 g of crude title compound as an oil, which was used as such.

Preparation of S-p-(2-methoxyethyl)phenyl glycidyl ether from
R-1-bromo-2-acetoxy-3-[p-(2-methoxyethyl)-phenyloxy]-propane A mixture of 3.65 g of crude R-1-bromo-2-acetoxy-3-[p-(2-methoxyethyl)-phenyloxy]-propane, 65 ml of dry 1,2-dimethoxyethane and 2.2 g (39.3 mmole) of powdered potassium hydroxide was stirred at 22° C. for 20 hours. After standing in the refrigerator for two days 1M sodium bicarbonate (50 ml) was added and the mixture was concentrated in vacuum and extracted with ether.

The extract was washed with 1M sodium bicarbonate and brine and dried with magnesium sulphate.

After filtration the filtrate was evaporated to give 2.04 g of an oil. This was purified over a Merck Fertigsäule C packed silica gel column with ether/hexane=1:1 and ether/ethanol=20:1 as the eluent. The fractions containing the epoxide were combined and evaporated to give 1.31 g of the title compound as an oil.

Preparation of
S-1-isopropylamino-3-[p-(2-methoxyethyl)-phenyloxy]-2-propanol (S-metoprolol) from
S-p-(2-methoxyethyl)phenyl glycidyl ether A mixture of 1.31 g (6.3 mmole) of S-p-(2-methoxyethyl)phenyl glycidyl ether, 10 ml of ethanol and 5 ml of isopropylamine was heated in a water bath of 55° C. for 1½ hours.

The mixture was evaporated to give 1.67 g of title compound as a solid. After derivatisation of a sample with the acid chloride of (+)-α-methoxy-α-trifluoromethyl-phenyl acetic acid the resulting amide showed in NMR the presence of only 0.7 wt % of the R-isomer.

EXAMPLE 7

*Rhodococcus erythropolis* SCL 38-2 (CBS 179.86) was grown in a 3 l fermentor in 1.5 l of 5× concentrated GYMB medium at an air supply of 90 l/h. The medium was stirred and kept at a pH of 6.8 to 7.2. As inoculum 15 ml of a 48 h old *Rhodococcus erythropolis* culture grown on a normal GYMB medium was used. After 65 h of growth the culture, having an optical density at 600 nm of 37 in a 1 cm pathlength cell of LKB Ultrospec 4050 was incubated with 15 g R,S-2,2-dimethyl-1,3-dioxolane-4-methanol during 4 h. Subsequently the pH was increased to 7.5 and kept constant by a 4N $NH_4OH$ supply during a feed containing 8M R,S-2,2-dimethyl-1,3-dioxolane-4-methanol (feed rate 2.2 g/h). The concentrations of R and S-2,2-dimethyl-1,3-dioxolane-4-methanol were assayed by elution of 3 ml fermentation broth over an Extrelut-3 column (Merck nr. 15372). At least 5 min. later the column was eluted with 12 ml ethyl acetate. This procedure gave a quantitative extraction of 2,2-dimethyl-1,3-dioxolane-4-methanol. Diastereoisomers of this alcohol were formed with BSTFA (see Example 5). The ratio of both enantiomers could be determined by use of a chiral complexation column (Table 4).

TABLE 4

The enantiomeric excess of R-2,2-dimethyl-1,3-dioxolane-4-methanol in a fermentation broth of *Rhodococcus erythropolis* supplied with a feed of a racemic mixture of this compound.

| h after start of the feed | ee of the R enantiomer |
|---|---|
| 0 | 0.43 |
| 20 | 0.94 |
| 26 | 0.97 |
| 29 | 0.97 | ee = enantiomeric excess

The feed was continued during 29 h. At that moment the broth contained 24.3 g/l of R-2,2-dimethyl-1,3-dioxolane-4-methanol and 0.37 g/l of the S-enantiomer. During the feed a constant production of acid was observed. The produced acid was identified as 2,2-dimethyl-1,3-dioxolane-4-carboxylic acid by means of NMR. The $^{13}C$ NMR spectrum exhibits the following signals:

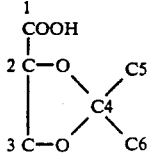

| | | δ (ppm/TMS) |
|---|---|---|
| | C1 | 180.11 |
| | C2 | 77.64 |
| | C3 | 69.49 |
| | C4 | 113.00 |
| | C5, C6 | 27.43, 27.03 |

TMS = tetra methylsilane

EXAMPLE 8

A 6 l culture of *Rhodococcus erythropolis* SCL 38-2 (CBS 179.86) was grown on medium 3310 in a 10 l fermentor. Cells were cultured at 30° C., the medium was stirred, air was supplied (360 l/h) and the pH was regulated between 6.8 and 7.2 by the addition of 4N $H_2SO_4$ or $NH_4OH$. The culture reached an optical density at 600 nm of 60 and at that moment 10 g/l R,S-2,2-dimethyl-1,3-dioxolane-4-methanol were added. After complete consumption of the S-enantiomer again 10 g/l R,S-2,2-dimethyl-1,3-dioxolane-4-methanol were added. The final alcohol obtained had an enantiomeric excess of the R-enantiomer of 0.97. The final broth (5.5 l) contained 47.0 g of 2,2-dimethyl-1,3-dioxolane-4-methanol.

EXAMPLE 9

Shake flasks of 2l, containing 500 ml of GYMB medium were inoculated with 10 ml of a 24 h culture of *Rhodococcus erythropolis* SCL 38-2 (CBS 179.86) grown on BHI medium in shake flasks. Cells were grown during 48 h at 30° C. The culture was induced by incubation in 5 g/l R,S-2,2-dimethyl-1,3-dioxolane-4-methanol during 5.5 h. Thereafter the cells were harvested by centrifugation and the pellets were resuspended in various buffers resulting in a concentration with a factor of 6 (see Table 5).

A volume of 100 ml of each suspension was transferred to a 500 ml baffled shake flask and R,S-2,2-dimethyl-1,3-dioxolane-4-methanol was added at various time points. The concentrations of R and S-2,2-dimethyl-1,3-dioxolane-4-methanol were assayed in an ethyl acetate extract of the suspension. The extraction rendement of this extraction was found to be 40%. The results presented in Table 5 show that resting cell suspensions can produce large quantities of R-2,2-dimethyl-1,3-dioxolane-4-methanol.

TABLE 5

Scheme of additions of R,S-2,2-dimethyl-1,3-dioxolane-4-methanol and measured excess of the R enantiomer during incubation of cell suspensions of various buffers.

| Suspensions | 0 | 24 | 42 | 50 | 73 | 90 | 162 | 167[4] | 194 | 236 | final conc. g/l[6] |
|---|---|---|---|---|---|---|---|---|---|---|---|
| a. 1M MOPS[1] pH = 7.5 | | | | | | | | | | | |
| additions | 3 g | — | — | 2.1 g | — | — | — | 0.25 g | 0.9 g | — | |
| e.e. | n.m. | 0.32 | 0.95 | n.m. | 0.60 | 0.68 | 0.90 | 0.90 | n.m. | 0.79 | 30.3 |
| b. 1M potassium phosphate pH = 7.5 | | | | | | | | | | | |
| additions | 3 g | — | — | — | — | — | — | 0.5 g | — | — | 15.7[5] |
| e.e. | n.m. | 0.07 | 0.13 | n.m. | 0.27 | 0.36 | 0.99 | 1.00 | n.m. | 1.00 | |
| c. 1M TRIS[2] pH = 7.5 | | | | | | | | | | | |
| additions | 3 g | — | — | — | — | 0.5 g | — | 0.25 g | — | — | 15.2 |
| e.e. | n.m. | 0.18 | 0.40 | n.m. | 0.84 | 0.86[3] | 0.94 | 0.95[3] | n.m. | 0.83 | |
| d. 1M TRIS[2] pH = 8.0 | | | | | | | | | | | |
| additions | 3 g | — | — | — | — | 0.5 g | — | 0.5 g | — | — | 18.1 |
| e.e. | n.m. | 0.18 | 0.42 | n.m. | 0.78 | 0.88[3] | 0.82 | 0.81[3] | n.m. | 0.69 | | n.m. = not measured
e.e. = enantiomeric excess
[1] MOPS = (3-[N-morpholino]propane sulfonic acid)
[2] TRIS = Tris (hydroxymethyl) aminomethane
[3] Before additions of a new quantity of R,S-2,2-dimethyl-1,3-dioxolane-4-methanol
[4] Incubation of cell suspensions a and c was continued with 50% of the original volume before additions of a new quantity of R,S-2,2-dimethyl-1,3-dioxolane-4-methanol
[5] at 210 h
[6] A 40% extraction rendement of the 1:1 ethyl acetate extraction for 2,2-dimethyl-1,3-dioxolane-4-methanol was assumed.

EXAMPLE 10

*Rhodococcus erythropolis* SCL 38-2 (CBS 179.86) was grown in a 10 l fermentor in 6 of 5× concentrated GYMB medium. The medium was stirred, aerated (360 l/h), kept at a temperature of 30° C. and a pH of 6.8 to 7.2. After 48 h of growth the culture, having an optical density of 30 was induced by a 5 h incubation with 10 g/l R,S 2,2-dimethyl-1,3dioxolane-4-methanol. The cells from the induced culture were harvested by centrifugation. A part of the obtained pellet was suspended in 1.5 l physiological salt (O.D. is 62) adjusted to a pH of 7.5 with 4N NaOH. The suspension was transferred to a 3 l fermentor vessel and incubated at 30° C., stirred and aerated with 90 l air/h. Addition of 1 g/l of R,S-2,2-dimethyl-1,3-dioxolane-4-methanol resulted in acidification. Two feeds containing 4N of NaOH and 8M R,S-2,2-dimethyl-1,3-dioxolane-4-methanol, respectively, were regulated automatically in the following way: the feeds ran with identical rate if the pH decreased below 7.5 and stopped if the pH increased above 7.5. The process continued during 99 h. Afterwards cells were spun down and resuspended in 1.5 l of fresh physiological salt and the feed of R,S-2,2-dimethyl-1,3-dioxolane-4-methanol and NaOH were regulated identically as described for the first run, now during 142 h. A third run was done under similar conditions during 92 h except for the final 21 h, when only NaOH was supplied upon pH decrease below 7.5. The results presented in Table 6 show that resting cell suspensions can produce enantiomeric pure R-2,2-dimethyl-1,3-dioxolane-4-methanol.

signment of the —$CH_3$ resonances to S and R-2,2-dimethyl-1,3-dioxolane-4-carboxylic acid rests upon the ration of converted R and S-2,2-dimethyl-1,3-dioxolane-4-methanol.

The exact position of the —$CH_3$ resonances may very with the amount of chiral solvating agent added.

EXAMPLE 12

A 48 h old 6 l culture of *Rhodococcus erythropolis* SCL 38-2 (CBS 179.86) obtained as described in Example 10 was incubated with 10 g/l of R,S-2,2-dimethyl-1,3-dioxolane-4-methanol during 6 h.

After the incubation cells and the culture fluid were separated by centrifugation and the cells were resuspended in 6 l of physiological salt adjusted to pH=7.5, which contained 15 g/l R,S-2,2-dimethyl-1,3-dioxolane-4-methanol. Two feeds containing 4N NaOH and 8M R,S,-2,2-dimethyl-1,3-dioxolane-4-methanol, respectively, were supplied during 29 h upon every pH decrease below 7.5, as described in Example 10.

TABLE 6

Concentrations and optical purities of R-2,2-dimethyl-1,3-dioxolane-4-methanol and 2,2-dimethyl-1,3-dioxolane-4 carboxylic acid.

| run | duration h | 2,2-dimethyl-1,3-dioxolane-4-methanol g/l[1] | ee (R-form) | 2,2-dimethyl-1,3-dioxolane-4-carboxylic acid g/l[2] |
|---|---|---|---|---|
| 1 | 99 | 60.7 | 0.81 | 73.5 |
| 2 | 142 | 38.6 | 0.90 | not measured |
| 3 | 92 | 13.2 | 0.99 | not measured | ee = enantiomeric excess
[1] The concentration of 2,2-dimethyl-1,3-dioxolane-4-methanol was determined as in Example 7.
[2] The concentration of 2,2-dimethyl-1,3-dioxolane-4-carboxylic acid was determined after quantitative conversion of this acid to glyceric acid. This was done by a 1 h incubation of the fermentation broth containing 2,2-dimethyl-1,3-dioxolane-4-carboxylic acid with $HClO_4$ during 1 h. After centrifugation the concentration of glyceric acid in the supernatant was assayed after elution of the supernatant over a HPLC cation exchanger (column: Aminex HPX 87 H Bio-Rad 125-0140).

EXAMPLE 11

A 48 h old 6 l culture of *Rhodococcus erythropolis* SCL 38-2 (CBS 179.86) obtained as described in Example 10 was incubated with 10 g/l of R,S-2,2-dimethyl-1,3-dioxolane-4-methanol during 6 h.

The induced culture was supplied with 30 g of R,S-2,2-dimethyl-1,3-dioxolane-4-methanol and after pH adjustment to 7.5 two feeds containing 4N NaOH and 8M R,S-2,2-dimethyl-1,3-dioxolane-4-methanol, respectively, were supplied upon every pH decrease below 7.5 as described in Example 10.

The process was continued during 52 h. The final broth contained 54.4 g/l of 2,2-dimethyl-1,3-dioxolane-4-carboxylic acid for the R-isomer (ee=0.92). The concentration of the acid was assayed as described in Example 10.

The measurement of the enantiomeric purity of 2,2-dimethyl-1,3-dioxolane-4-carboxylic acid was based on splitting of the —$CH_3$ signals in the NMR spectrum of the acid in the presence of an excess of R-(+)-1-(1-naphthyl) ethyl amine. Two methyl signals appear at 1.30 and 1.15 ppm respectively (due to the S-enantiomer) and two methyl signals appear at 1.10 and 1.05 ppm, respectively, (due to the R-enantiomer). The as- The final cell suspension contained 27.9 g/l of 2,2-dimethyl-1,3-dioxolane-4-carboxylic acid with an enantiomeric excess of 0.88. The concentration and optical purity of the acid were assayed as described in Example 11.

EXAMPLE 13

Shake flasks of 2 l containing 500 ml GYMB medium were inoculated with 10 ml of a 24 h culture of *Rhodococcus erythropolis* SCL 38-2 (CBS 179.86) grown on BHI medium in shake flasks. Cells were grown during 48 h at 30° C. The culture was induced by incubation in 5 g/l R,S-2,2dimethyl-1,3-dioxolane-methanol during 6 h.

Cells originating from 1 liter of culture were resuspended in either 250 ml 1M MOPS buffer (pH=7.5) or 250 ml 1M potassium phosphate buffer (pH=7.5). The obtained suspensions were transferred to 2 l baffled shake flasks and R,S-2,2-dimethyl-1,3-dioxolane-4-methanol was added at various time points. The concentrations of R and S-2,2-dimethyl-1,3-dioxolane-4carboxylic acid were assayed as described in Example 11.

The results presented in Table 7 show that resting cell suspensions can produce large quantities of R-2,2-dimethyl-1,3-dioxolane-4-carboxylic acid.

TABLE 7

Scheme of additions of R,S-2,2-dimethyl-1,3-dioxolane-4-methanol and measured excess of the R enantiomer of the produced 2,2-dimethyl-1,3-dioxolane-4-carboxylic acid during incubation of cell suspensions of various buffers.

| Suspensions | time (h) | | | | | | | final conc. g/l |
|---|---|---|---|---|---|---|---|---|
| | 0 | 1 | 17 | 41 | 48 | 72 | 89 | 160 |
| a. 1M MOPS pH = 7.5 | | | | | | | | |

TABLE 7-continued

Scheme of additions of R,S-2,2-dimethyl-1,3-dioxolane-4-methanol and measured excess of the R enantiomer of the produced 2,2-dimethyl-1,3-dioxolane-4-carboxylic acid during incubation of cell suspensions of various buffers.

| Suspensions | time (h) | | | | | | | | final conc. g/l |
|---|---|---|---|---|---|---|---|---|---|
| | 0 | 1 | 17 | 41 | 48 | 72 | 89 | 160 | |
| additions | 6.1 g | 1.9 g | 1.8 g | — | 1.5 g | 1.6 g | — | — | |
| e.e. | n.m. | n.m. | 0.92 | 0.92 | n.m. | n.m. | 0.88 | 0.88 | 24.2 |
| b. 1M potassium phosphate pH = 7.5 | | | | | | | | | |
| additions | 6.1 g | 2.0 g | 1.9 g | — | — | — | — | — | 11.0 |
| e.e. | n.m. | n.m. | n.m. | n.m. | n.m. | n.m. | 0.90 | 0.90 | | n.m. = not measured
e.e. = enantiomeric excess
MOPS = (3-[N-morpholino]propane sulfonic acid)

EXAMPLE 14

Shake flask cultures of *Rhodococcus erythropolis* SC1-38-2 (CBS 179.86) were grown on GYMB medium during 48 h and subsequently incubated with 5 g/l of R,S-2,2-dimethyl-1,3-dioxolane-4-methanol during 5 h. The induced cultures were centrifuged and the cell pellet was divided in 4 parts. The parts A, B and C were suspended separately in physiological salt, one part D was suspended in physiological salt containing 10% glycerol. Suspension C was lyophilized. Samples A and C were incubated during 28 days at 4° C., B and D at −18° C. After the incubation sample C was resuspended in the original volume of physiological salt. The other suspensions were thawed. Cells of all obtained suspensions were spun down and resuspended in 100 ml of 1M MOPS (see Example 9) pH =7.5 containing 10 g/l of R,S-2,2-dimethyl-1,3-dioxolane-4-methanol. The optical densities at 600 nm of all suspensions were 28. The suspensions were transferred to 500 ml baffled shake flasks and incubated in a shaker at 30° C. The increase of the enantiomeric excess of R-2,2-dimethyl-1,3-dioxolane-4-methanol shows that the cells are still able to convert the S-enantiomer of this compound (see Table 8).

TABLE 8

Enantiomeric excess of R-2,2-dimethyl-1,3-dioxolane-4-methanol in cell suspensions conserved in various ways.

| conservation temperature | further manipulations | ee of R-2,2-dimethyl-1,3-dioxolane-4-methanol | | | |
|---|---|---|---|---|---|
| | | after 1 h | 2 h | 3 h | 4 h |
| T = 4° C. | — | 0.05 | 0.11 | 0.16 | 0.22 |
| T = 4° C. | lyophilized | 0.06 | 0.10 | 0.14 | 0.21 |
| T = −18° C. | — | 0.03 | 0.08 | 0.11 | 0.15 |
| T = −18° C. | 10% glycerol | 0.07 | 0.15 | 0.23 | 0.34 |

EXAMPLE 15

The micro-organisms listed in Table 9 were grown for 48 hours at 30° C. in 100 ml baffle flasks containing 25 ml of GYMB/MOPS medium. To a concentrated GYMB-medium a solution of MOPS [3-(N-morpholino)propane sulfonic acid], pH 7.0, was added, such that a 100 mM buffer was obtained in an original GYMB-medium.

To the grown cultures about 4.8 g/l RS-2,2-dimethyl-1,3-dioxolane-4-methanol was added and the cultures were incubated further for 8, 24 and 48 hours. At each time point indicated two cultures of each micro-organism were extracted with an equal volume of ethyl acetate. By doing so an extraction recovery of about 40% of the 2,2-dimethyl-1,3-dioxolane-4-methanol present was obtained. The extracted compound from each culture separately was then derivatised and analysed on a chiral complexation column as described in Example 5. The results are presented in Table 9.

TABLE 9

| Incubation period | 8 h | | | 24 h | | | 48 h | | |
|---|---|---|---|---|---|---|---|---|---|
| Micro-organism | g/l* | % R | % S | g/l* | % R | % S | g/l* | % R | % S |
| Corynebacterium spec. T 1300/CBS 267.87 | n.d. | n.d. | n.d. | 1.3 | 98 | 2 | 1.2 | 100 | 0 |
| Mycobacterium rhodochrous/NCIB 11061 | 2.3 | 50 | 50 | 1.4 | 87 | 13 | 1.0 | 100 | 0 |
| Nocardia aurantia NCIB 9557 | 0.91 | 100 | 0 | 0.84 | 100 | 0 | 0.47 | 100 | 0 |
| Nocardia calcarea NCIB 8863 | 1.7 | 76 | 24 | 1.2 | 100 | 0 | 0.97 | 100 | 0 |
| Nocardia cathaarde T 985/CBS 268.87 | 2.0 | 53 | 47 | n.d. | n.d. | n.d. | 1.0 | 99 | 1 |
| Nocardia globerula NCIB 9159 | 1.7 | 59 | 41 | 1.1 | 100 | 0 | 1.4 | 100 | 0 |
| Nocarida ragosa NCIB 8926 | 2.4 | 54 | 46 | 0.63 | 99 | 1 | 0.54 | 100 | 0 |
| Corynebacterium alkanum ATCC 21194 | 1.2 | 82 | 18 | 0.32 | 100 | 0 | 0.16 | 100 | 0 |
| Corynebacterium equi A 2362 (CBS 264.87) | 2.2 | 53 | 47 | 0.95 | 99 | 1 | 0.86 | 99 | 1 |
| Corynebacterium equi A 2431 (CBS 263.87) | 1.4 | 74 | 26 | 0.81 | 100 | 0 | 0.62 | 100 | 0 |
| Corynebacterium- | 1.6 | 61 | 49 | 0.83 | 100 | 0 | 0.41 | 100 | 0 |

TABLE 9-continued

| Incubation period | 8 h | | | 24 h | | | 48 h | | |
|---|---|---|---|---|---|---|---|---|---|
| Micro-organism | g/l* | % R | % S | g/l* | % R | % S | g/l* | % R | % S |
| *hydrocarboclastus* ATCC 15108 | | | | | | | | | |
| *Corynebacterium* sp. DS 5122 (CBS 265.87) | 1.9 | 56 | 44 | 0.90 | 100 | 0 | 0.74 | 100 | 0 |
| *Nocardia canicruria* ATCC 31548 | 0.91 | 100 | 0 | 0.50 | 100 | 0 | 0.27 | 100 | 0 |
| *Nocardia corallina* ATCC 31338 | 1.7 | 5.9 | 41 | 0.85 | 100 | 0 | 0.45 | 100 | 0 |
| *Nocardia erythropolis* T 487/NCIB 9158 | 1.7 | 67 | 33 | 0.68 | 100 | 0 | 0.58 | 100 | 0 |
| *Nocardia erythropolis* DSM 743 | 1.3 | 95 | 5 | 1.1 | 100 | 0 | 0.61 | 100 | 0 |
| *Nocardia erythropolis* ATCC 4277 | 1.2 | 98 | 2 | 0.84 | 99 | 1 | 0.55 | 99 | 1 |
| *Nocardia paraffinae* NCIB 11277 | 2.2 | 53 | 47 | 0.86 | 99 | 1 | 0.48 | 99 | 1 |
| Nocardia spec. DS 5123 (CBS 266.87) | 1.8 | 63 | 37 | 0.98 | 100 | 0 | 0.72 | 100 | 0 |
| *Rhodococcus erythropolis* SCL 38-2/CBS 179.86 | 1.2 | 89 | 11 | 0.86 | 99 | 1 | 0.61 | 99 | 1 |
| *Rhodococcus rhodochrous* NCIB 9703 | 1.2 | 88 | 12 | 0.59 | 99 | 1 | 0.24 | 99 | 1 |
| *Rhodococcus rhodochrous* ATCC 21197 | 2.2 | 50 | 50 | 0.89 | 99 | 1 | 0.60 | 99 | 1 |

All values presented are the mean of a duplicate result.
*The extracted quantities presented are not corrected for losses caused by a poor extraction recovery.

EXAMPLE 16

The micro-organisms listed in Table 10 were grown as described in Example 15. However instead of RS-2,2-dimethyl-1,3-dioxolane-4-methanol now about 2.4 or 4.8 g/l RS-2,2-pentylene-4-hydroxymethyl-1,3-dioxolane (glycerol cyclohexanon derivative) was added to the grown cultures. The incubation proceeded for 24 to 48 hours. Extraction, derivatisation and analysis were as described in Examples 5 and 11.

The extraction recovery of the glycerol cyclohexanon derivative was estimated at 100%.

Preparation of 2,2-pentylene-4-hydroxymethyl-1,3-dioxolane

A stirred mixture of 100 ml (0.96 mole) of cyclohexanone, 130 ml (2.08 mole) of glycerol, 300 ml of hexane and 5 g of 4-toluenesulphonic acid monohydrate was refluxed while separating the condensed waterlayer for 20 hours. After the addition of 4 ml of triethyl amine, the mixture was concentrated in vacuum and the residue shaken water/diethyl ether. The waterlayer was extracted with diethyl ether and the combined ether extracts were washed with 30% sodium chloride, dried with magnesium sulphate, filtered and evaporated to give 153 g of residue. This was vacuumdistilled to give 113.6 g of title compound.

TABLE 10

| | g/l substrate added | Incubation period 24 h | | | Incubation period 48 h | | |
|---|---|---|---|---|---|---|---|
| Micro-organism | | g/l extracted | % R | % S | g/l extracted | % R | % S |
| *Corynebacterium equi* A 2431 (CBS 263.87) | 4.8 | n.d. | | | 3.1 | 81 | 19 |
| *Nocardia erythropolis* ATCC 4277 | 2.4 | n.d. | | | 0.43 | 100 | 0 |
| *Rhodococcus equi* IFO 03730 | 2.4 | n.d. | | | 1.4* | 94 | 6 |
| *Rhodococcus rhodochrous* NCIB 9703 | 4.8 | 1.5 | 100 | 0 | n.d. | | |
| *Rhodococcus rhodochrous* ATCC 21197 | 2.4 | n.d. | | | 0.5 | 91 | 7 |

All values presented are the mean of a duplicate result except for * which value was obtained from a single experiment.
n.d. = not determined.

EXAMPLE 17

The microorganisms listed in Table 11 were grown as described in Examples 15 and 16. Now 2,2-butylene-4-hydroxymethyl-1,3-dioxolene-4-methanol (glycerol cyclopentanon derivative) was added to the grown cultures. The cultures were further incubated for 24 and 48 hours. Extraction, derivatisation and analysis were as described before.

The extraction recovery of the glycerolcyclopentanon derivative was estimated at 100%.

Preparation of 2,2-butylene-4-hydroxymethyl-1,3-dioxolane4-methanol

A mixture of 88 ml (1 mole of cyclopentanone, 140 ml (2.24 mole) of glycerol, 300 ml of hexane and 5 g of 4-toluenesulphonic acid monohydrate was stirred and refluxed while separating the condensed waterlayer for 28 hours. After cooling and the addition of 4 ml of triethyl amine the mixture was concentrated in vacuum and shaken with diethyl ether/water. The waterlayer was extracted with diethyl ether (3×) and the combined ether extracts were washed with water and brine, dried with magnesium sulphate and evaporated to give 117 g of residue. This was vaccumdistilled to give 105 g of the title compound.

TABLE 11

| Micro-organism | g/l substrate added | Incubation period 24 h | | | Incubation period 48 h | | |
|---|---|---|---|---|---|---|---|
| | | g/l extracted | % R | % S | g/l extracted | % R | % S |
| Corynebacterium alkanum ATCC 21194 | 4.8 | 1.6 | 88 | 12 | 0.66 | 91 | 9 |
| Nocardia paraffinae NCIB 11277 | 4.8 | n.d. | | | 1.6 | 100 | 0 |
| Rhodococcus erythropolis SCL 38-2/CBS 179.86 | 2.4 | 0.57 | 100 | 0 | n.d. | | |
| Rhodococcus rhodochrous NCIB 9703 | 4.8 | 2.4 | 99 | 1 | 1.8 | 100 | 0 |
| Rhodococcus rhodochrous ATCC 21197 | 4.8 | n.d. | | | 2.3 | 97 | 3 |

All values presented are the mean of a duplicate result.
n.d. = not determined.

EXAMPLE 18

*Rhodococcus rhodochrous* strain NCIB 9703 and strain ATCC 21197 were grown as described in Examples 15 and 16. Now 2,2-diethyl-4-hydroxy-methyl-1,3-dioxolane (glycerol pentanon derivative) was added to the grown culture and further incubated for 24 hours. Extraction, derivatisation and analysis were as described before.

The extraction recovery of the glycerol pentanon derivative was estimated at 100%.

The results are presented in Table 12.

Preparation of 2,2-diethylene-4-hydroxymethyl-1,3-dioxolane-4-methanol

A stirred mixture of 85 ml (0.805 mole) of 3-pentanone, 104 ml (1.68 mole) of glycerol, 250 ml of hexane and 4 g of 4-toluenesulphonic acid monohydrate was refluxed while separating the condensed waterlayer for 18 hours. After cooling 4 ml of triethyl amine was added and the mixture was concentrated in vacuum. The residue was shaken with diethyl ether/water. The waterlayer was extracted twice with diethyl ether (3×) and the combined extracts were washed with water and brine, dried with magnesium sulphate, filtered and evaporated to give 48 g of residue. This was vacuumdistilled to give two fractions of 11.50 g and 6.12 g, respectively, of the title compound.

TABLE 12

| Micro-organism | g/l substrate added | Incubation period 24 h | | |
|---|---|---|---|---|
| | | g/l extracted | % R | % S |
| Rhodococcus rhodochrous NCIB 9703 | 2.4 | 0.8 | 100 | 0 |
| | 4.8 | 2.2 | 100 | 0 |
| Rhodococcus rhodochrous ATCC 21197 | 2.4 | 1.5 | 70 | 30 |

All values presented are the mean of a duplicate result.

EXAMPLE 19

*Corynebacterium equi* A 2431, CBS 263.87, spec. DS 5122, CBS 265.87 and *Nocardia spec.* DS 5123, CBS 266.87 were grown as described before in Example 15 and 16. Now 2.4 g/l of 4-hydroxymethyl-1,3-dioxolane (glycerolformaldehyde derivative) were added to the grown cultures. The cultures were then further incubated for 6 hours. Thereafter the cells were separated from the broth by centrifugation and the supernatant eluted over an Exterlyt-3-column (Merck nr. 15372). Thereafter the column was eluted with ethyl acetate for a GC-analysis. The extraction recovery using this procedure is estimated at 50%. The results are presented in Table 13.

TABLE 13

| Micro-organism | GC-Analysis | | |
|---|---|---|---|
| | g/l extracted | % R | % S |
| Cornyebacterium equi A 2431/CBS 263.87 | 0.22 | 68 | 32 |
| Cornebacterium spec. DS 5122/CBS 265.87 | 0.15 | 82 | 18 |
| Nocardia spec. DS 5123 CBS 266.87 | 0.035 | 100 | 0 |

Preparation of (R,S)-4-hydroxymethyl-1,3-dioxolane

A mechanically stirred mixture of 104 g (0.78 mole) of (R,S)-2,2-dimethyl-4-hydroxymethyl-1,3-dioxolane, 500 ml of benzene, 86 g (1.53 mole) of powdered potassium hydroxide and 175 ml (1.52 mole) of benzyl chloride was refluxed for 17 hours while separating the condensed waterlayer (14 ml of water separated). After cooling the mixture was washed with water, 1M sodium hydrogen carbonate and brine respectively, dried with magnesium sulphate, filtered and evaporated to give 287 g of crude benzyl ether. This was stirred with a mixture of 300 ml of methanol, 100 ml of water and 20 ml of 36% hydrochloric acid for 1,5 hours. Next the mixture was neutralized with about 10 g of sodium hydroxide in water and concentrated in vacuum. The residue was extracted with diethyl ether and the extract was dried with magnesium sulphate, filtered and evaporated to give 163 g of residue. This was purified over silica to give 118 g of (R,S)-3-benzyloxy-propane-1,2-diol.

18.2 g (0.1 mole) of this was mixed with 50 ml of hexane, 10 g of paraformaldehyde and 0.5 g of paratoluenesulphonic acid monohydrate and stirred and refluxed for 4 hours while separating the condensed waterlayer. After cooling the mixture was washed with 1M sodium hydrogen carbonate and brine, filtered and evaporated to give 17.78 g of (R,S)-4-benzyloxymethyl-1,3-dioxolane. This was mixed with 100 ml of diethyl ether and 1.5 g of 10% palladium on carbon and stirred under atmospheric hydrogen for 4 hours. Next the catalyst was filtered off and the filtrate was evaporated and purified over silica with diethyl ether to give 8.07 g of the title compound.

EXAMPLE 20

*Rhodococcus erythropolis* SCL 38-2 (CBS 179.86) and *Rhodococcus rhodochrous* ATCC 21197 were grown for 48 hours as described before (see Example 15). To some of the grown cultures about 4.8 g/l R,S-2,2-dimethyl-1,3-dioxolane-4-methanol were added and incubated further for about 5 hours, to induce the enzymatic activity normally responsible for the resolution of the R,S-2,2-dimethyl-1,3-dioxolane-4-methanol. Cells from the induced culture were then harvested by centrifugation, washed with 100 mM MOPS-buffer pH 7.0 and collected twice concentrated in 100 mM of the same buffer and samples of 25 ml were put in 100 ml baffle flasks. About 5.0 g/l R,S-2,2-pentylene-4-hydroxymethyl-1,3-dioxolane (glycerolcyclohexanon derivative) were added to the suspensions and they were further incubated overnight at 30° C. The suspensions were then extracted and analysed as described before (see Example 15 and 16). The results presented in Table 14 show that the induced cells are able to convert stereospecifically the glycerolcyclohexanon derivative, whereas the non-induced cells do not or only very slowly attack the compound. A control experiment in which non-induced cells were also suspended and incubated with the two compounds mentioned showed that no degradation took place.

TABLE 14

| Micro-organism | Conditions | Substrate dimethyl derivative (1) | | | Substrate cyclohexanon derivative (2) | | |
|---|---|---|---|---|---|---|---|
| | | g/l extracted | % R | % S | g/l extracted | % R | % S |
| *Rhodococcus erythropolis* SCL 38-2 CBS 179.86 | Normal assay (3) incubation period t = 5 h | 1.4 | 57 | 43 | | | |
| | T = 24 h | 0.96 | 100 | 0 | 5.4 | 51 | 49 |
| | Induced cells in buffer. Incubation overnight. | 0.90 | 100 | 0 | 3.2 | 81 | 19 |
| *Rhodococcus rhodochrous* ATCC 21197 | Normal assay (3) incubation period t = 5 h | 2.2 | 52 | 48 | | | |
| | t = 24 h | 1.1 | 100 | 0 | 6.9 | 52 | 48 |
| | Induced cells in buffer. Incubation overnight. | 0.61 | 100 | 0 | 4.1 | 76 | 24 |

All values presented are the mean of a duplicate result.
(1) dimethyl derivative = R,S-2,-dimethyl-1,3-dioxolane-4-methanol. An extraction recovery of about 40% is assumed. The extracted quantities are not corrected for losses caused by a poor extraction recovery.
(2) cyclohexanon derivative = R,S-2,2-pentylene-4-hydroxymethyl-1,3-dioxolane. An extraction recovery of about 100% is assumed.
(3) Normal assay is the procedure as used in Example 15 and 16.

EXAMPLE 21

A similar experiment as described in Example 20 was performed with *Nocardia canicruria* ATCC 31548, in which cells induced with R,S-2,2-dimethyl-1,3-dioxolane-4-methanol were suspended in MOPS-buffer. Now, however the substrate to be resolved, added to the suspensions, was R,S-2,2-diethyl-4-hydroxymethyl-1,3-dioxolane (glycerolpentanon derivative). The result of this experiment is presented in Table 15. (The same control experiment as described in Example 20 has also been performed using this substrate.)

TABLE 15

| Micro-organism | Conditions | Substrate dimethyl derivative (1) | | | Substrate pentanon derivative (2) | | |
|---|---|---|---|---|---|---|---|
| | | g/l extracted | % R | % S | g/l extracted | % R | % S |
| *Nocardia canicruria* ATCC 31548 | Normal assay (3) incubation period t = 5 h | 1.3 | 72 | 28 | | | |
| | t = 24 h | n.d. (4) | n.d. | n.d. | 6.6 | 47 | 53 |
| | Induced cells in buffer. Incubation overnight. | 0.75 | 100 | 0 | 3.7 | 85 | 15 |

All values presented are the mean of a duplicate result.
(1) dimethyl derivative = R,S-2,2-dimethyl-1,3-dioxolane-4-methanol. An extraction recovery of about 40% is assumed. The extracted quantities are not corrected for losses caused by a poor extraction recovery.
(2) pentanon derivative = R,S-diethyl-4-hydroxymethyl-1,3-dioxolane.
(3) Normal assay is the procedure as used in Example 15 and 16.
(4) n.d. = not determined in this particular experiment.

EXAMPLE 22

*Corynebacterium equi* (CBS 263.87) and *Rhodococcus equi* (IFO 0370) were grown as described before in Example 15 and 16. Now 2.4 g/l of the asymmetric compound 2-methyl-2-isobutyl-4-hydroxymethyl-1,3-dioxolane (glycerolmethylisobutylketon derivative) were added to the grown cultures. The cultures were further incubated for 48 hours. Thereafter extraction was performed using methyl trichloride and the samples prepared for NMR-analysis. With NMR the four enantiomers could be resolved and the ratios between the enantiomers were determined. The signals originating from the two R-isomers (i.e. R for the configuration of the $C_2$ of the glycerol part of the derivative) could be denominated by using a glycerolmethylisobutylketon derivative synthesized from R-2,2-dimethyl-1,3-dioxolane-4-methanol as a reference compound.

The results are presented in Table 16. This example shows that asymmetric derivatives can also be resolved.

TABLE 16

| Micro-organism | g/l extracted | percentage of the various enantiomers present | | | |
|---|---|---|---|---|---|
| | | R*/... % | S*/... % | R*/... % | S*/... % |
| Corynebacterium equi/CBS 263.87 | 1.1 | 39 | 0 | 46 | 15 |
| Rhodococcus equi IFO 03730 | 1.8 | 35 | 2 | 35 | 28 |

The values presented are the mean of a duplicate experiment.
*The first R or S denomination of the 4 enantiomers (R,R, R/S, S/R and S/S) concerns the $C_2$ of the glycerol part of the derivative. Which signal originates from the R/R enantiomer and which from the R/S was not determined.

Preparation of
R,S-2-methyl-2-isobutyl-4-hydroxymethyl-1,3-dioxolane

A mixture of 65 ml (0.517 mole) of methylisobutylketone, 200 ml of hexane, 70 ml (1.12 mole) of glycerol and 3 g of 4-toluenesulphonic acid monohydrate was stirred and refluxed while separating the condensed waterlayer for 48 hours. After cooling triethyl amino (4 ml) was added and the mixture was evaporated in vacuum and shaken with diethyl ether/water. The waterlayer was extracted (2×) with diethyl ether and the combined ether extracts were washed with water and brine, dried with magnesium sulphate, filtered and evaporated to give 70 g of residue. This was vacuumdistilled to give 62 g of title compound.

Preparation of
2-methyl-2-isobutyl-4-(R)-hydroxymethyl-1,3-dioxolane

A stirred mixture of 5.48 ml (41.5 mmole) of (R)-(−)-2,2-dimethyl-4-hydroxymethyl-1,3-dioxolane (e.e.=0.9), 50 ml of benzene, 4.6 g of powdered potassium hydroxide and 10 ml of benzyl chloride was refluxed over molesieve 4A for 23 hours. After cooling the mixture was washed with water, 1M sodium hydrogen carbonate and brine respectively, filtered and evaporated. The residue was stirred with a mixture of 15 ml of methanol, 5 ml of water and 1 ml of 36% hydrochloric acid for 1½ hours. Next the mixture was neutralized with sodium hydroxide, evaporated and extracted with diethyl ether. The extract was dried with magnesium sulphate, filtered and evaporated to give 9.40 g of oil. This was purified over silica to give 6.59 g of (S)-3-benyloxy-propane-1,2-diol.

A mixture of 0.4 g of this, 10 ml of benzene, 1 ml of methylisobutyl ketone and 30 mg of paratoluenesulphonic acid was refluxed for 18 hours over molesieve 4A. After cooling triethyl amine (50 ml) was added and the mixture was washed with water, filtered and evaporated. The residue was mixed with 10 ml of diethyl ether, 0.1 ml of triethyl amine and 0.2 g of 10% palladium on carbon and stirred under atmospheric hydrogen for 12 hours. The mixture was filtered and the filtrate was evaporated to give 0.34 g of the title compound, contaminated with the benzyl ether.

EXAMPLE 23

Nocardia paraffinae NCIB 11277 was grown as described before in Example 15 and 16. Now 2.4 g/l of the asymmetric compound 2-methyl-4-hydroxymethyl-1,3-dioxolane (glycerolacetaldehyde derivative) were added to the culture and further incubated for 15 hours. The cells were then separated from the broth by centrifugation and the supernatant eluted over an Exterlyt-3-column. Thereafter the column was eluted with ethyl acetate for a GC-analysis with which the four enantiomers could be separated. By using this procedure about 80% of the added substrate left over was extracted. As in Example 22 the R-isomers (i.e. R for the configuration of the $C_2$ of the glycerol part of the derivative) could be denominated by using a glycerolacetaldehyde derivative synthesized from R-2,2-dimethyl-1,3-dioxolane-4-methanol as a reference compound.

The result is presented in Table 17.

As in Example 22 this result also shows that asymmetric derivatives can be resolved.

Preparation of R,S-2-methyl-4-hydroxymethyl-1,3-dioxolane (racemic acetaldehyde derivative)

A mixture of 70 ml of paracetaldehyde, 400 ml of hexane, 200 ml of glycerol and 5.4 g of paratoluenesulphonic acid monohydrate was stirred and refluxed for 3×24 hours while separating the condensed waterlayer. After cooling triethyl amine (5 ml) was added and the mixture was concentrated in vacuum and the residue was vacuumdistilled (65°–84° C./1.5–3 mm Hg) giving 129.74 g of a mixture of the title compound and 2-methyl-5-hydroxy-1,3-dioxolane.

About 50 g of this was chromatographed twice over silica with diethyl ether as the eluent giving 9.45 g of racemic title compound, contaminated with 7.5% of 2-methyl-5-hydroxy-1,3-dioxolane.

Preparation of
2-methyl-4-(R)-hydroxymethyl-1,3-dioxolane
(R-acetaldehyde derivative)

A mixture of 0.47 g (2.58 mmole) of (S)-3-benzyloxy-propane-1,2-diol, 10 ml of hexane, 0.4 ml of paracetaldehyde and 15 mg of paratoluenesulphonic acid monohydrate was stirred and refluxed over molesieve 4A for 1.5 hours. After cooling a drop of triethyl amine was added and the mixture was washed with water, filtered and evaporated.

The residue was mixed with 10 ml of diethyl ether and 0.15 g of 10% palladium on carbon and stirred under atmospheric hydrogen for 3 hours. The mixture was filtered and evaporated to give 195 mg of the title compound.

TABLE 17

| Micro-organism | g/l extracted (1) | percentage of the various enantiomers present | | | |
|---|---|---|---|---|---|
| | | R*/... % (2) | S*/... % (2) | R*/... % (2) | S*/... % (2) |
| Nocardia paraffinae | 0.22 | 61 | 9 | 30 | 0 |

TABLE 17-continued

| Micro-organism | g/l extracted (1) | percentage of the various enantiomers present | | | |
|---|---|---|---|---|---|
| | | R*/... % (2) | S*/... % (2) | R*/... % (2) | S*/... % (2) |
| NCIB 11277 | | | | | |

All values presented are the mean of a duplicate result.
(1) Not corrected for losses during recovery.
(2) The first R or S denomination of the 4 enantiomers (R/R, R/S, S/R and S/S) concerns the $C_2$ of the glycerol part of the derivative. Which GC-peak originates from the R/R enantiomer and which from the R/S was not determined.

We claim:

1. Process for the preparation of 2,2-$R_1$,$R_2$-1,3-dioxolane-4methanol enriched in R-isomer wherein $R_1$ and $R_2$ are H or alkyl groups, optionally branched, or wherein $R_1$ and $R_2$ together with the carbon atom to which they are attached form a carbocyclic ring which comprises subjecting a mixture of R- and S-2,2-$R_1$,$R_2$-1,3-dioxolane-4-methanol to the action of a bacteria selected from the group consisting of the genus Nocardia, the genus Rhodococcus, the genus Corynabacterium and the genus Mycobacterium having the ability for stereoselective consumption of S-2,2-$R_1$,$R_2$-1,3dioxolane-4-methanol for a period of time such that S-2,2-$R_1$,$R_2$-1,3-dioxolane-4-methanol in the mixture is altered to give a 2,2-$R_1$,$R_2$-1,3-dioxolane-4-methanol enriched in R-isomer.

2. Process according to claim 1 wherein the period of time is such that at least 80% of S-2,2-$R_1$,$R_2$-1,3-dioxolane-4-methanol is altered.

3. Process according to claim 2 wherein the period of time is such that at least 90% of S-2,2-$R_1$,$R_2$-1,3-dioxolane-4-methanol is altered.

4. Process according to claim 1 wherein substantially pure R-2,2-$R_1$,$R_2$-1,3-dioxolane-4-methanol is produced.

5. Process according to claim 1 wherein the alkyl groups contain less than 6 carbon atoms or wherein the carbocyclic ring contains less than 8 carbon atoms.

6. Process according to claim 1 wherein $R_1$ and $R_2$ are identical.

7. Process according to claim 1 wherein $R_1$ and $R_2$ are H or an alkyl group containing 1-3 carbon atoms or together with the carbon atom to which they are attached form a carbocyclic ring containing 5 or 6 carbon atoms.

8. Process according to claim 1 wherein the microorganism used in Rhodococcus equi selected from the group consisting of Rhodococcus equi NCIB 12035 or Rhodococcus equi (IFO 03730).

9. Process according to claim 1 wherein the microorganism used is Rhodococcus rhodochrous selected from the group consisting of Rhodococcus rhodochrous (NCIB 9703) or Rhodococcus rhodochrous (ATCC 21197).

10. Process according to claim 1 wherein the microorganism used is Rhodococcus erythropolis selected from the group consisting of Rhodococcus erythropolis SCL 38-2 (CBS 179.86) Rhodococcus erythropolis SCL 38-2R (CBS 180.86) or Rhodococcus erythropolis SCL 38-2S (CBS 181.86).

11. Process according to claim 1 wherein the microorganism used is Corynebacterium equi selected from the group consisting of Corynebacterium equi A 2362 (CBS 264.87) or Corynebacterium equi A 2431 (CBS 263.87).

12. Process according to claim 1 wherein the microorganism used is Corynebacterium alkanum (ATCC 21194).

13. Process according to claim 1 wherein the microorganism used is Corynebacterium hydrocarboclastus (ATCC 15108).

14. Process according to claim 1 wherein the microorganism used is Corynebacterium sp. DS 5122 (CBS 265.87) or Corynebacterium sp. T 1300 (CBS 267.87).

15. Process according to claim 1 wherein the microorganism used is Nocardia erythropolis selected from the group consisting of Nocardia erythropolis T 487 (NCIB 9158), Nocardia erythropolis (DSM 743) or Nocardia erythropolis (ATCC 4277).

16. Process according to claim 1 wherein the microorganism used is Nocardia corallina (ATCC 31338).

17. Process according to claim 1 wherein the microorganism used is Nocardia canicruria (ATCC 31548).

18. Process according to claim 1 wherein the microorganism used is Nocardia paraffinae (NCIB 11277).

19. Process according to claim 1 wherein the microorganism used is Nocardia spec. DS 5123 (CBS 266.87).

20. Process according to claim 1 wherein the microorganism used is Nocardia aurantia (NCIB 9557).

21. Process according to claim 1 wherein the microorganism used is Nocardia calcarea (NCIB 8863).

22. Process according to claim 1 wherein the microorganism used is Nocardia cathaarde T 985 (CBS 268.87).

23. Process according to claim 1 wherein the microorganism used is Nocardia globerula (NCIB 9159).

24. Process according to claim 1 wherein the microorganism used is Nocardia ragosa (NCIB 8926).

25. Process according to claim 1 wherein the microorganism used is Mycobacterium rhodochrous (NCIB 11061).

26. Process according to claim 1 wherein said bacteria is immobilized either as a living cell, as a killed cell or as a resting cell.

27. Process according to claim 1, wherein the S-2,2-$R_1$,$R_2$-1,3-dioxolane-4-methanol is substantially converted into R-2,2-$R_1$,$R_2$-1,3-dioxolane-4-carboxylic acid.

28. The process of claim 1, wherein $R_1$ and $R_2$ are methyl groups, and wherein the process further comprises a step wherein the R-isomer enriched product is converted to metaprolol enriched in the S isomer.

29. The process of claim 27, further comprising the steps of separating the R-isomer enriched 2,2-$R_1$,$R_2$-1,3-dioxolane-4-carboxylic acid from the R-isomer enriched 2,2-$R_1$,$R_2$-dioxolane-4-methanol, and converting the R-isomer enriched 2,2-$R_1$$R_2$-1,3dioxolane-4-carboxylic acid into S-isomer enriched 2,2-$R_1$$R_2$-dioxolane-4-methanol.

* * * * *